United States Patent [19]

Davis et al.

[11] Patent Number: 5,512,267

[45] Date of Patent: Apr. 30, 1996

[54] ZEOLITE CIT-1

[75] Inventors: Mark E. Davis; Raul F. Lobo, both of Pasadena, Calif.

[73] Assignee: California Institute of Technology, Pasadena, Calif.

[21] Appl. No.: 306,177

[22] Filed: Sep. 14, 1994

Related U.S. Application Data

[63] Continuation-in-part of Ser. No. 121,748, Sep. 15, 1993, abandoned.

[51] Int. Cl.$^6$ .......................... C01B 39/04; C01B 39/12; C01B 39/46; C01B 39/48
[52] U.S. Cl. .......................... 423/705; 423/706; 423/718; 423/713; 502/62; 502/77; 208/46; 585/400; 585/407
[58] Field of Search .................................. 423/704, 705, 423/706, 718; 502/62, 77; 208/46; 585/400, 407

[56] References Cited

U.S. PATENT DOCUMENTS

| | | | |
|---|---|---|---|
| 3,140,249 | 7/1964 | Plank et al. | 208/120 |
| 3,140,251 | 7/1964 | Plank et al. | 208/120 |
| 3,140,253 | 7/1964 | Plank et al. | 208/120 |
| 4,049,573 | 9/1977 | Kaeding | 502/77 |
| 4,269,813 | 5/1981 | Klotz | 423/277 |
| 4,508,837 | 4/1985 | Zones | 502/62 |
| 4,528,171 | 7/1985 | Casci et al. | 423/718 |
| 4,544,538 | 10/1985 | Zones | 423/706 |
| 4,550,092 | 10/1985 | Chang et al. | 502/71 |
| 4,554,142 | 11/1985 | Hoelderich et al. | 423/277 |
| 4,559,315 | 12/1985 | Chang et al. | 502/71 |
| 4,610,854 | 9/1986 | Zones | 423/706 |
| 4,623,526 | 11/1986 | Leen | 502/77 |
| 4,661,467 | 4/1987 | Kuehl | 502/77 |
| 4,665,110 | 5/1987 | Zones | 423/706 |
| 4,701,313 | 10/1987 | Chang et al. | 423/277 |
| 4,910,006 | 3/1990 | Zones et al. | 423/706 |
| 4,963,337 | 10/1990 | Zones | 423/277 |
| 5,110,570 | 5/1992 | Bellussi et al. | 423/705 |
| 5,166,111 | 11/1992 | Zones et al. | 502/64 |
| 5,200,377 | 5/1993 | Zones et al. | 502/62 |
| 5,254,514 | 10/1993 | Nakagawa | 502/62 |

FOREIGN PATENT DOCUMENTS

| | | |
|---|---|---|
| 0040016 | 11/1981 | European Pat. Off. . |
| 0188913 | 7/1986 | European Pat. Off. . |
| WO91/09907 | 7/1991 | WIPO ............................. C08L 33/08 |

OTHER PUBLICATIONS

Sieber et al "Formation & Properties of Losod, a New Sodium Zeolite," *Helvetica Chemica Acta* vol. 57, #6 1975 (no month) pp. 1533–1549.

*Primary Examiner*—Mark L. Bell
*Assistant Examiner*—David Sample
*Attorney, Agent, or Firm*—Limbach & Limbach

[57] ABSTRACT

A zeolite composition CIT-1 is provided, the composition having a mole ratio greater than about 20:1 of a first oxide selected from silicon oxide, germanium oxide, or mixtures thereof to a second oxide comprising boron oxide; which zeolite composition has a specific X-ray powder diffraction pattern in accordance with Table 1 of the disclosure. In one embodiment, the second oxide may comprise mixtures of boron oxide with one or more of aluminum oxide, gallium oxide, iron oxide, titanium oxide and vanadium oxide. Also disclosed is a method for making CIT-1 zeolites comprising the preparation of an aqueous mixture containing sources of a N,N,N-trimethyl cis-myrtanyl ammonium ion, boron oxide or mixtures of boron oxide with one or more of aluminum oxide, gallium oxide, iron oxide, titanium oxide and vanadium oxide, and an oxide selected from silicon oxide, germanium oxide, and mixtures thereof. The mixture is maintained under sufficient crystallization conditions, preferably at a temperature of at least 100° C., in an autoclave and under autogenous pressure until the crystals of the zeolite are formed.

22 Claims, 4 Drawing Sheets

ZEOLITE CIT-1

This application is a continuation-in-part of U.S. application Ser. No. 08/121,748, filed Sep. 15, 1993, now abandoned.

BACKGROUND OF THE INVENTION

Natural and synthetic zeolitic crystalline aluminosilicates are useful as catalysts and adsorbents. These aluminosilicates have distinct crystal structures which are demonstrated by X-ray diffraction. The crystal structure defines cavities and pores which are characteristic of the different species. The adsorptive and catalytic properties of each crystalline aluminosilicate are determined in part by the dimensions of its pores and cavities. Thus, the utility of a particular zeolite in a particular application depends at least partly on its crystal structure.

Because of their unique molecular sieving characteristics, as well as their catalytic properties, crystalline aluminosilicates are especially useful in such applications as gas drying and separation and hydrocarbon conversion. Although many different crystalline aluminosilicates and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogenous zeolites" have been prepared from reaction mixtures containing an organic templating agent, usually a nitrogen-containing organic cation. By varying the synthesis conditions and compositions of the reaction mixture, different zeolites can be formed using the same templating agent. Use of N,N,N-trimethyl cyclopentylammonium iodide in the preparation of Zeolite SSZ-15 molecular sieve is disclosed in U.S. Pat. No. 4,610,854; use of 1-azoniaspiro[4.4] nonyl bromide and N,N,N-trimethyl neopentylammonium iodide in the preparation of a molecular sieve termed "Losod" is disclosed in Helv. Chim. Acta (1974); vol. 57, p. 1533 (W. Sieber and W. M. Meier); use of quinuclidinium compounds to prepare a zeolite termed "NU-3" is disclosed in European Patent Publication No. 40016; use of 1,4-di( 1-azoniabicyclo [2.2.2.]octane) lower alkyl compounds in the preparation of Zeolite SSZ-16 molecular sieve is disclosed in U.S. Pat. No. 4,508,837; use of N,N,N-trialkyl-1-adamantamine in the preparation of Zeolite SSZ-13 molecular sieve is disclosed in U.S. Pat. No. 4,544,538, and for SSZ-24 in U.S. Pat. No. 4,665,110.

Synthetic zeolitic crystalline borosilicates are useful as catalysts. Methods for preparing high silica content zeolites that contain framework boron are known and disclosed in U.S. Pat. No. 4,269,813. The amount of boron contained in the zeolite usually may be made to vary by incorporating different amounts of borate ion in the zeolite forming solution.

The use of quaternary ammonium compound in the preparation of a boron-containing zeolite is disclosed in European Patent Application No. 188,913. A method for treating a zeolite containing aluminum and boron with a silicon substitution treatment is disclosed in U.S. Pat. No. 4,701,313.

SUMMARY OF THE INVENTION

The present invention relates to a novel stable synthetic crystalline material characterized as a borosilicate, aluminosilicate or boroaluminasilicate which is prepared using N,N,N-trimethyl cis-myrtanyl ammonium salt as the template. This novel synthetic crystalline material is referred to herein as "CIT-1" and has a specified X-ray diffraction pattern. The present invention also relates to the preparation of CIT-1.

Thus, according to the present invention, a zeolite composition CIT-1 is provided, the composition having a mole ratio greater than about 20:1 of a first oxide selected from silicon oxide, germanium oxide, or mixtures thereof to a second oxide selected from boron oxide or mixtures of boron oxide with one or more of with aluminum oxide, gallium oxide, iron oxide, titanium oxide and vanadium oxide; which zeolite composition has, after calcination, a specific X-ray powder diffraction pattern in accordance with Table 1 provided below.

In one embodiment, the zeolite of the invention contains greater than 100 ppm of boron or a mixture of boron and one or more of aluminum, gallium, iron, titanium or vanadium.

In accordance with the present invention, there is also provided a zeolite composition having a mole ratio greater than about 20:1 of a first oxide selected from silicon oxide, germanium oxide and mixtures thereof to a second oxide selected from aluminum oxide, gallium oxide, iron oxide, titanium oxide, vanadium oxide and mixtures thereof, which zeolite composition has, after calcination, the X-ray diffraction pattern in accordance with Table I below.

The CIT-1 zeolite preferably has a composition, as synthesized and in the anhydrous state, in terms of mole ratios of oxides as follows: (1.0 to 5) $Q_2O$: (0.1 to 1.0) $M_2O$: $W_2O_3$: (greater than 20) $YO_2$ wherein M is an alkali metal cation, W is boron or a mixture of boron with one or more of aluminum, gallium, iron, titanium and vanadium, Y is selected from silicon, germanium and mixtures thereof, and Q is a N,N,N-trimethyl cis-myrtanyl ammonium ion.

In another preferred embodiment, the amount of boron or boron mixture is between 0.3 and 1.5% by weight, and most preferably about 0.7% by weight.

As used herein, the terms "ppm" and "wt %" refer to the amount by weight of the specified element, e.g., boron (as opposed to boron oxide), present in CIT-1 based on the weight of the anhydrous, calcined zeolite.

According to one embodiment of the present invention, a method is provided for making CIT-1 zeolites, comprising preparing an aqueous mixture containing sources (1) of a N,N,N-trimethyl cis-myrtanyl ammonium ion, (2) boron oxide or mixtures of boron oxide with one or more of aluminum oxide, gallium oxide, iron oxide, titanium oxide and vanadium oxide, and (3) an oxide selected from silicon oxide, germanium oxide, and mixtures thereof. The aqueous mixture has a composition, in terms of mole ratios of oxides falling within the following ranges:

|  | Broad | Preferred |
|---|---|---|
| $YO_2/W_2O_3$ | 20–200 | 30–60 |
| $OH/YO_2$ | 0.10–1.0 | 0.20–0.30 |
| $Q/YO_2$ | 0.05–0.50 | 0.10–0.25 |
| $M+/YO_2$ | 0.05–0.50 | 0.05–0.20 |
| $Q/Q+M+$ | 0.30–0.80 | 0.40–0.70 | wherein Y is selected from silicon, germanium, and mixtures thereof, W is boron or mixtures of boron with one or more of aluminum, gallium, iron, titanium and vanadium, and Q is a N,N,N-trimethyl cis-myrtanyl ammonium ion. The mixture is maintained at a temperature of at least 100° C. in an autoclave and under autogenous pressure until the crystals of the zeolite are formed and the crystals are recovered.

BRIEF DESCRIPTION OF THE FIGURES

The invention will be better understood by reference to the appended figures in which.

DETAILED DESCRIPTION OF THE PREFERRED EMBODIMENT

Zeolites SSZ-26 (described in U.S. Pat. No. 4,910,006) and SSZ-33 (described in U.S. Pat. No. 4,963,337) have some similarities to the zeolite of the present invention as evidenced by the similarities between the X-ray diffraction patterns of such prior art zeolites when compared with the X-ray diffraction pattern of CIT-1. The method of making SSZ-26 and SSZ-33 cannot, however, be used to make CIT-1. Successful preparation of the boron containing CIT-1 structure requires use of a new synthesis as described herein.

SSZ-26 and SSZ-33 are molecular sieves which contain a three-dimensional pore system comprised of intersecting 10- and 12-ring pores. These two zeolites can be characterized as members of a family of materials in which the two end members are formed by the stacking of layers in an ABAB . . . sequence or an ABCABC . . . sequence. The framework formed by the ABAB . . . stacking sequence ("polymorph A") is of orthorhombic symmetry and the framework formed by the ABCABC . . . stacking sequence ("polymorph B") is of monoclinic symmetry. In between these end-member polymorphs there is a whole family of materials that can be characterized by a fault probability p. If the fault probability is p=0%, the end member polymorph B is obtained, and if p=100%, the end member polymorph A is obtained. The aluminosilicate SSZ-26 and the borosilicate SSZ-33 are members of this family of materials with fault probabilities of approximately 15% and 30% respectively.

Zeolite CIT-I is a new zeolite borosilicate which is the pure monoclinic polymorph ("polymorph B") of this family of materials.

Figure 2:
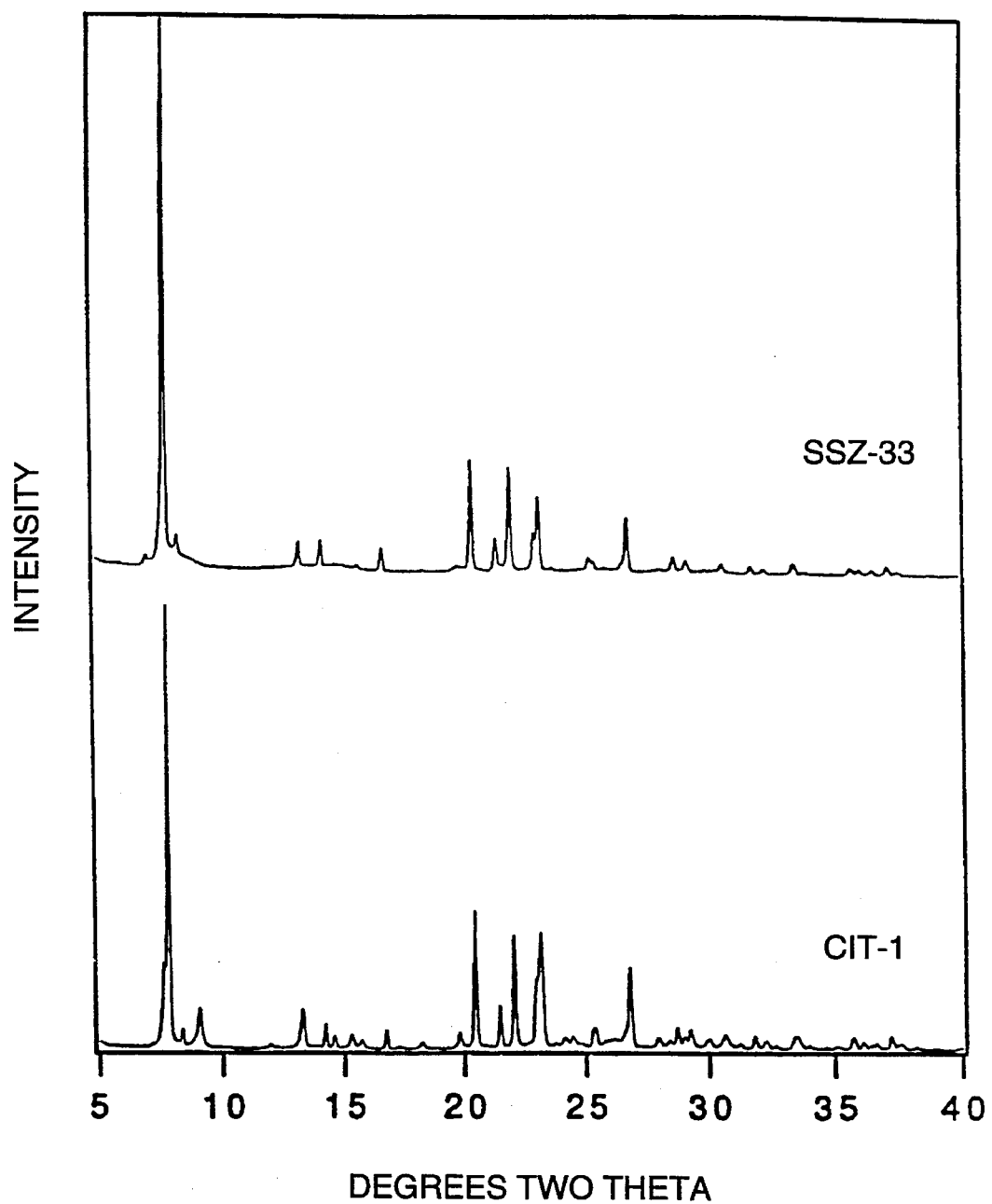
FIG. 2 compares the X-ray powder diffraction patterns of CIT-1 and SSZ-33.

CIT-1 zeolites have a crystalline structure having the characteristic X-ray powder diffraction pattern provided in Table 1. A more complete X-ray powder diffraction pattern for CIT-1 is provided in Table 1A. Although SSZ-33 has almost the same X-ray diffraction pattern as SSZ-26 (see U.S. Pat. No. 4,963,337), the X-ray diffraction pattern of CIT-1 shows many differences. In addition to the lines present in the pattern of SSZ-33, CIT-1 shows numerous other lines. In Tables 1 and 1A, the lines that are present for CIT-1 that are not present in the X-ray diffraction pattern of SSZ-33 are marked with an asterisk. The characteristic lines of SSZ-33 are shown in Table 2. FIG. 2, from which the data for CIT-1 in Table 1 is taken, is a comparison of the two X-ray diffraction patterns of SSZ-33 and CIT-1. The presence of the additional lines in the X-ray diffraction pattern of CIT-1 has allowed us to identify the atomic structure of this material. The approximate atomic coordinates for CIT-1 are given in Table 3.

The X-ray diffraction patterns of calcined samples of SSZ-33 and CIT-1 in FIG. 2 show some similarities in the patterns of the two zeolites. However, in spite of these similarities, there are significant differences below 20° 2θ between the patterns. These differences arise from differences in the long range order of the crystalline structures. SSZ-33 is a disordered structure with a fault probability of 30%. Comparisons of the experimental to the simulated XRD patterns of these materials show very good agreement between experimental and simulated patterns. There is also good agreement between the unit cell dimensions of the borosilicates SSZ-33 and CIT-1 (polymorph B). The calculated unit cell for SSZ-33 (polymorph A) is a=21.08Å, b=13.26Å, c=12.33Å; and for SSZ-33 (polymorph B) is a=22.62Å, b=13.26Å and c=12.33Å, β=68.7.

The presence of many lines which are equivalent in both X-ray diffraction patterns of SSZ-33 and CIT-1 is, however, indicative of similarities in their corresponding structures, and gives rise to the expectation that CIT-1 will have outstanding catalytic properties similar to those of SSZ-33 which is useful in hydrocarbon conversion, e.g. reforming, processes.

TABLE 1 d-spacing and indexing for calcined CIT-1

| d/(Å) | Intensity[1] | hkl[2] | | |
|---|---|---|---|---|
| 11.50* | VS | 0 | 0 | 1 |
| 11.26 | VS | 1 | 1 | 0 |
| 9.75* | M | 2 | 0 | 1 |
| 7.38* | W | 1 | 1 | −1 |
| 6.39* | W | 3 | 1 | 1 |
| 6.06* | W | 2 | 0 | 2 |
| 5.77* | W | 0 | 0 | 2 |
| 5.11* | M | 3 | 1 | 2 |
| 4.86* | W | 4 | 0 | 2 |
| 4.48* | M−W | 2 | 2 | 2 |
| 4.33 | S | 1 | 3 | 0 |
| 4.13 | W | 4 | 2 | 0 |
| 4.02 | S | 5 | 1 | 0 |
| 3.87 | S | 3 | 1 | 3 |
| 3.69* | W | 2 | 2 | −2 |
| 3.64* | W | 6 | 0 | 2 |
| 3.59* | W | 4 | 2 | −1 |
| 3.32 | M | 0 | 4 | 0 |
| 3.19* | W | 0 | 4 | −1 |
| 3.14* | W−M | 2 | 4 | 1 |
| 3.08* | W | 2 | 0 | 4 |

[1]The X-ray patterns are based on a relative intensity scale in which the stronger line in the X-ray pattern is assigned a value of 100: W (weak) is less than 20; M (medium) is between 20 and 40, S (strong) is between 40 and 60; VS (very strong) is greater than 60.
[2]Monoclinic: a = 22.62 Å, b = 13.28 Å, c = 12.38 Å, β = 68.9°.
*Peaks present in in CIT-1 which are not present in SSZ-33.

TABLE 1A d-spacing and indexing for calcined CIT-1

| d/(Å) | 100 × $I/I_o$[a] | hkl[b] | | |
|---|---|---|---|---|
| 11.50* | 66 | 0 | 0 | 1 |
| 11.26 | 100 | 1 | 1 | 0 |
| 10.57 | 10 | 2 | 0 | 0 |
| 9.75* | 26 | 2 | 0 | 1 |
| 7.38* | 2 | 1 | 1 | −1 |
| 6.69 | 3 | 2 | 0 | −1 |
| 6.64 | 12 | 0 | 2 | 0 |
| 6.39* | 2 | 3 | 1 | 1 |
| 6.22 | 7 | 3 | 1 | 0 |
| 6.06* | 4 | 2 | 0 | 2 |
| 5.77* | 7 | 0 | 0 | 2 |
| 5.62 | 3 | 4 | 0 | 1 |

TABLE 1A-continued d-spacing and indexing for calcined CIT-1

| d/(Å) | 100 × I/I$_o$[a] | hkl[b] | | |
|-------|-----------------|---|---|---|
| 5.28  | 6  | 4 | 0 | 0 |
| 5.11* | 22 | 3 | 1 | 2 |
| 4.86* | 3  | 4 | 0 | 2 |
| 4.48* | 21 | 2 | 2 | 2 |
| 4.33  | 53 | 1 | 3 | 0 |
| 4.13  | 18 | 4 | 2 | 0 |
| 4.02  | 44 | 5 | 1 | 0 |
| 3.87  | 49 | 3 | 1 | 3 |
| 3.84  | 55 | 4 | 0 | 3 |
| 3.75  | 1  | 3 | 3 | 0 |
| 3.69* | 5  | 2 | 2 | −2 |
| 3.64* | 6  | 6 | 0 | 2 |
| 3.59* | 2  | 4 | 2 | −1 |
| 3.51  | 12 | 2 | 2 | 3 |
| 3.45  | 3  | 5 | 1 | −1 |
| 3.34  | 15 | 4 | 0 | −2 |
| 3.32  | 27 | 0 | 4 | 0 |
| 3.19* | 4  | 0 | 4 | −1 |
| 3.14* | 18 | 2 | 4 | 1 |
| 3.11  | 7  | 6 | 2 | 0 |
| 3.08* | 4  | 2 | 0 | 4 |
| 3.05  | 15 | 5 | 3 | 0 |

[a]Calculated as the ratio of the peak area and the peak area of the 1 1 0 reflection.
[b]Monoclinic: a = 22.62 Å, b = 13.28 Å, c = 12.38 Å, β = 68.9°.
*Peaks present in CIT-1 which are not present in SSZ-33.

X-ray diffraction patterns were determined by standard techniques. The patterns were collected with a computer controlled diffractometer using Cu-Kα radiation and a solid-state Ge detector cooled with liquid nitrogen. All reflections were individually deconvoluted to obtain accurate peak positions and widths. From these measured values, the relative intensities, 100 I/I$_o$, where I$_o$ is the intensity of the strongest line or peak and d, the interplanar spacing in Angstroms corresponding to the deconvoluted lines, can be calculated.

The X-ray diffraction patterns of Tables 1 and 1A are characteristic of calcined CIT-1 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-boron mole ratio from sample to sample. Calcination can also cause minor shifts in the X-ray diffraction pattern. Notwithstanding these minor perturbations, the basic crystal lattice structure remains unchanged.

TABLE 2

SSZ-33

| 2θ | dÅ | Int. | 100 × I/I$_o$ |
|-----|------|------|------|
| 7.81  | 11.32 | 175  | 100 |
| 8.33  | 10.61 | 8    | 5 |
| 13.28 | 6.67  | 11   | 6 |
| 14.18 | 6.25  | 11   | 6 |
| 15.71 | 5.641 | 3    | 2 |
| 16.73 | 5.299 | 9    | 5 |
| 20.43 | 4.347 | 80   | 46 |
| 20.76 | 4.279 | 4    | 2 |
| 21.44 | 4.144 | 15   | 9 |
| 22.02 | 4.037 | 72   | 41 |
| 23.00 | 3.867 | 24 Sh | 14 Sh |
| 23.18 | 3.837 | 49   | 28 |
| 23.67 | 3.759 | 2    | 1 |
| 25.27 | 3.524 | 14   | 8 |
| 25.46 | 3.498 | 6 Sh | 3 Sh |
| 26.57 | 3.355 | 33   | 19 |
| 26.80 | 3.326 | 54   | 31 |
| 28.68 | 3.113 | 13   | 7 |
| 29.18 | 3.060 | 13   | 7 |
| 30.66 | 2.916 | 9    | 5 |
| 31.81 | 2.813 | 8    | 5 |
| 32.31 | 2.771 | 4    | 2 |
| 33.51 | 2.674 | 9    | 5 |
| 33.95 | 2.640 | 2    | 1 |
| 35.74 | 2.512 | 7    | 4 |
| 36.11 | 2.487 | 5    | 3 |
| 36.60 | 2.455 | 5    | 3 |
| 37.21 | 2.416 | 8    | 5 |
| 37.60 | 2.392 | 4    | 2 |

Figure 3A:
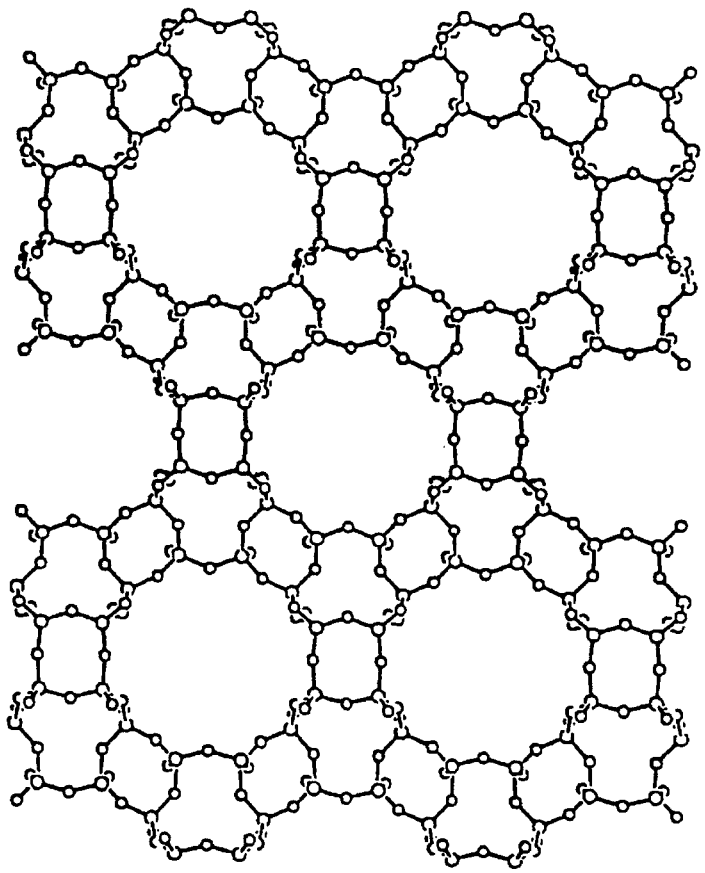
FIGS. 3A and 3B are "ball and stick" representations of the CIT-1 framework viewed approximately along [0 0 1] (3A), and along [0 1 0] (3B)
Figure 3B:
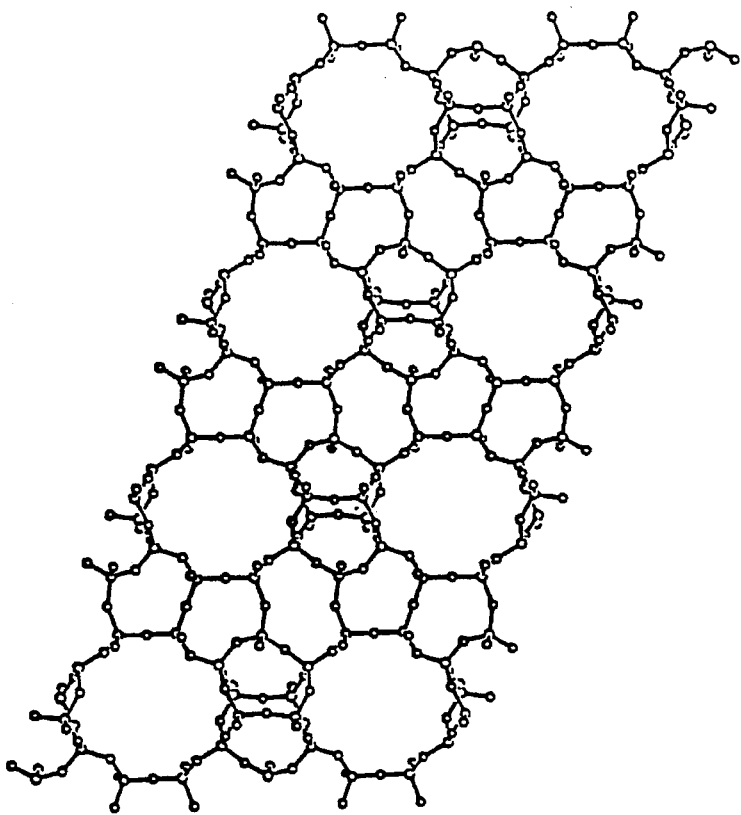

Based on the approximate atomic coordinates of Table 3, the ball and stick style representation of the CIT-1 framework structure is shown in FIGS. 3A and 3B. In FIG. 3A the view along [0 0 1] shows that CIT-1 has a large pore (12-ring) along the c axis. In FIG. 3b the view along [0 10] shows that CIT-1 has a medium pore (10-ring) along the b axis.

CIT-1 zeolites can be suitably prepared from an aqueous solution containing sources (1) of an alkali metal oxide; (2) N,N,N-trimethyl cis-myrtanyl ammonium ion; (3) boron oxides or mixtures of boron oxide and other oxides mentioned above; and (4) an oxide of silicon or germanium, or mixture of the two. The reaction mixture should have a composition in terms of mole ratios falling within the following ranges:

| | Broad | Preferred |
|---|---|---|
| YO$_2$/W$_2$O$_3$ | 20–200 | 30–60 |
| OH/YO$_2$ | 0.10–1.0 | 0.20–0.30 |
| Q/YO$_2$ | 0.05–0.50 | 0.10–0.25 |
| M+/YO$_2$ | 0.05–0.50 | 0.05–0.20 |
| Q/Q+M+ | 0.30–0.80 | 0.40–0.70 | wherein Q is N,N,N-trimethyl cis-myrtanyl ammonium ion, Y is silicon, germanium or both, and W is boron or mixtures of boron with one or more of aluminum, gallium, iron, titanium and vanadium. M is an alkali metal, preferably sodium.

Thus, CIT-1 zeolites preferably have a YO$_2$:W$_2$O$_3$ mole ratio greater than about 20:1 and can be made essentially alumina free. As prepared, the silica:boron oxide (or boron oxide mixture) ratio can be in the range of 20:1 to about 100:1. Higher mole ratios can be obtained by treating the zeolite with chelating agents or acids to extract boron from the zeolite lattice. The silica:boron oxide mole ratio can also be increased by using silicon and carbon halides and other similar compounds.

The N,N,N-trimethyl cis-myrtanyl ammonium ion component Q of the crystallization mixture is derived from the corresponding salt, depicted below, wherein A⁻ is an anion that does not interfere with the formation of the zeolite.

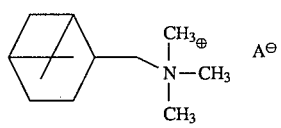

Preparation of N,N,N-trimethyl cis-myrtanyl ammonium ion is described in Example 1. Typically, the anion may be a hydroxide, acetate, sulfate, carboxylate or halide. Hydroxide is the preferred anion since it may be useful in ion exchange.

The reaction mixture is prepared using standard zeolitic preparation techniques. Sources of boron for the reaction mixture include borosilicate glasses and other reactive boron oxides. These include borates, boric acid and borate esters. Typical sources of silicon oxide include fumed silica, silicates, silica hydrogel, silicic acid, colloidal silica, tetra-alkyl orthosilicates, and silica hydroxides.

The reaction mixture is maintained under sufficient crystallization conditions, and at an elevated temperature, until the crystals of the zeolite are formed. The temperatures during the hydrothermal crystallization step should be no less than 100° C., since temperatures below this will result in impractical crystallization times. For this reason it is preferred that the temperature be maintained at from about 120° C. to about 200° C., and more preferably at from about 150° C. to about 175° C. The crystallization period is typically greater than 1 day and preferably from about 7 days to about 28 days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. from 8 to 24 hours, to obtain the as synthesized, CIT-1 zeolite crystals. The drying step can be performed at atmospheric or subatmospheric pressures.

During the hydrothermal crystallization step, the CIT-1 crystals can be allowed to nucleate spontaneously from the reaction mixture. The reaction mixture can also be seeded with CIT-1 crystals both to direct, and accelerate the crystallization, as well as to minimize the formation of undesired borosilicate contaminants.

CIT-1 zeolites will be used as thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:boron mole ratio. The zeolite can also be steamed since steaming helps stabilize the crystalline lattice to attack from acids. The zeolite could be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, Fe, and Co are generally preferred.

The hydrogen, ammonium, and metal components can be exchanged into the zeolite. The zeolite can also be impregnated with the metals, or, the metals can be physically intimately admixed with the zeolite using standard methods known to the art. And, some metals can be occluded in the crystal lattice by having the desired metals present as ions in the reaction mixture from which the CIT-1 zeolite is prepared.

Typical ion exchange techniques involve contacting the synthetic zeolite with a solution containing a salt of the desired replacing cation or cations. Although a wide variety of salts can be employed, chlorides and other halides, nitrates, acetates, and sulfates are particularly preferred. Representative ion exchange techniques are disclosed in a wide variety of patents including U.S. Pat. Nos. 3,140,249, 3,140,251 and 3,140,253, each of which is incorporated by reference.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product expected to be especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

As with other zeolites, it is expected that CIT-1 can be formed into a wide variety of physical shapes. Generally speaking, zeolites can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, CIT-1 would be extruded before drying, or, dried or partially dried and then extruded. Zeolites can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e, combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which could be composited with the synthetic zeolites of this invention include the montmorillonite and kaolin families, which families include the sub-bentonites and the kaolins commonly known as Dixie, McNamee, Georgia, and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, it is expected that the CIT-1 zeolites could be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia, as well as ternary compositions such as silica-alumina-thoria, silica-aluminazironcia, silica-alumina-magnesia, and silica-magnesia-zirconia. In such composites, the matrix can be in the form of a cogel.

It is further expected that the CIT-1 zeolites could also be composited with other zeolites such as synthetic and natural faujasites (e.g., X and Y), erionites, mordenites and also with purely synthetic zeolites such as those of the ZSM series. The combination of zeolites could also be composited in a porous inorganic matrix.

The boron in the crystalline network of CIT-1 may also be replaced either completely or in part by aluminum (see Example 7) using the procedures described in U.S. Pat. Nos. 4,559,315 and 4,550,092 which are hereby incorporated by reference.

CIT-1 zeolites are useful in hydrocarbon conversion reactions, such as the cracking of paraffin. Hydrocarbon conversion reactions are chemical and catalytic processes in which carbon containing compounds are changed to different carbon containing compounds. Examples of hydrocarbon conversion reactions in which CIT-1 is expected to be useful include catalytic cracking, and reforming. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, alkylating, isomerizing polyalkyl substituted aromatics (e.g., m-xylene), and disproportionating aromatics (e.g., toluene) to provide mixtures of benzene, xylenes and higher methylbenzenes, oxidation reactions, hydrocracking, dewaxing, and olefin and aromatics formation reactions.

CIT-1 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired the formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

CIT-1 can be used in hydrocarbon conversion reactions with active or inactive supports, with organic or inorganic binders, and with and without added metals. These reactions are well know to the art, as are the reaction conditions.

Aromatics Formation

CIT-1 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 10 bar, and liquid hourly space velocities (LHSV) ranging from 0.1 to 15.

The conversion catalyst preferably contains a Group VIII metal compound to have sufficient activity for commercial use. By "Group VIII metal compound" as used herein it is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753, issued May 31, 1994 to Nakagawa, for a description of such methods.

The preferred alkali metals are sodium, potassium, and cesium. The zeolite itself can be substantially free of acidity only at very high silica:alumina mole ratios.

Catalytic Cracking

Hydrocarbon cracking stocks can be catalytically cracked in the absence of hydrogen using CIT-1 at liquid hourly space velocities from 0.5 to 50, temperatures from about 260° F. to 1625° F. and pressures from subatmospheric to several hundred atmospheres, typically from about atmospheric to about 5 atmospheres.

For this purpose, the CIT-1 catalyst can be composited with mixtures of inorganic oxide supports as well as traditional cracking catalyst.

When CIT-1 is used as a catalytic cracking catalyst in the absence of hydrogen, the catalyst may be employed in conjunction with traditional cracking catalysts, e.g., any aluminosilicate heretofore employed as a component in cracking catalysts.

Examples of these traditional cracking catalysts are disclosed in U.S. Pat. No. 4,910,006 and U.S. Pat. No. 5,316,753. When a traditional cracking catalyst (TC) component is employed, the relative weight ratio of the TC to the CIT-I is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component. See the aforementioned U.S. Pat. No. 4,910,006 and U.S. Pat. No. 5,316,753 for examples of such matrix components.

The following examples illustrate the preparation of CIT-1. Further objectives and advantages of the present invention other than those set forth above will become apparent from the examples which are not intended to limit the scope of the present invention.

EXAMPLE 1

Preparation of N,N,N-Trimethyl cis-myrtanyl Ammonium (Template)

10 g of (−) cis myrtanyl amine (Aldrich) were dissolved in 100 ml of methanol to which 27 g of potassium carbonate ($K_2CO_3$, Aldrich) and 55 g of iodomethane (Aldrich) were added. The solution was stirred at room temperature in the absence of light for 48 hours. The reaction solution was then filtered and the solvent and excess iodomethane were evaporated in vacuum. The solid product remaining in the round flask was then extracted with 150 ml of $CHCl_3$, and the liquid extract filtered and evaporated in vacuum again. The white solid was recrystallized from ethanol at 4° C. to give 16.8 g of trimethylmyrtanyl ammonium iodide (Yield 80%). The organic template was further purified by recrystallization in acetone:methanol (9:1) solution. The iodide form of the template (6.54 g) was exchanged to the hydroxide form in a column with 100 ml of Amberlite IRA-400 (obtained from Aldrich). The solution of trimethylmyrtanyl ammonium hydroxide was concentrated to a total volume of 100 ml in a rotavap. By titration with 0.05M HCl, a concentration of 0.18M (90% exchange) of trimethylmyrtanyl ammonium hydroxide was calculated.

EXAMPLE 2

Preparation of CIT-1

CIT-1, a borosilicate zeolitic material was synthesized from a gel of composition:

50 $SiO_2$:1 $B_2O_3$:10 R OH:5 NaOH:5000 $H_2O$ where R is N,N,N-trimethyl cis-myrtanyl ammonium. The gel was prepared as follows: 0.05 g of sodium borate ($Na_2B_4O_7$ 10 $H_2O$, Fisher Scientific) and 0.1 g of sodium hydroxide 50% (Fisher Scientific) were added to a solution of 14 ml of trimethylmyrtanyl ammonium hydroxide (0.18M) and 8.5 ml of distilled water. After the sodium borate crystals were completely dissolved, 0.75 g of fumed silica (Cab-O-Sil M-5, Cabot Corp.) were added to the solution and the mixture was stirred until it was completely homogeneous. Finally, 10 mg of crystals of as-synthesized boron zeolite beta were added to the synthesis gel and stirred until the crystals were homogeneously dispersed.

The synthesis gel was then charged into pure-silica glass tubes (12 mm outside diameter, 85 mm long), the tubes were sealed and statically heated at 175° C. in a convection oven for 7 days. After the crystals were formed, the mixture was filtered, washed with distilled water and dried at room temperature overnight.

EXAMPLE 3

Characterization of CIT-1

The crystalline material obtained in Example 2 was characterized by thermogravimetric analysis and X-ray powder diffraction (Cu-Kα radiation). The thermogravimetric analysis (heating rate of 5° C. min⁻) showed a weight loss of 2.5% below 100° C., indicative of a small water loss as expected from a hydrophobic high-silica material. Additionally it showed a 12.5% weight loss after 350° C., characteristic of the combustion of the organic template inside the pores of the zeolite.

Figure 1:
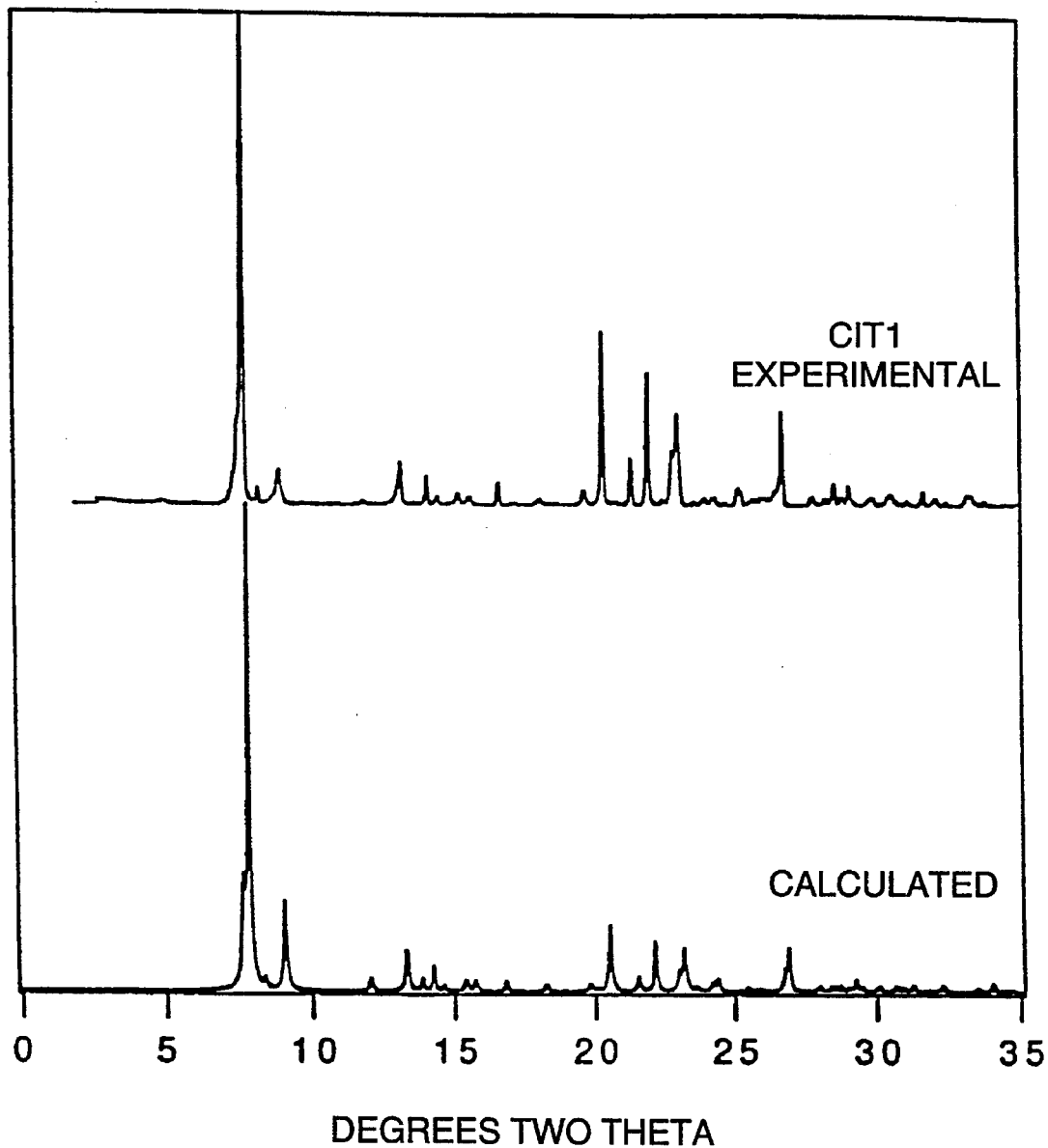
FIG. 1 depicts the x-ray powder diffraction pattern of a calcined sample of CIT-1, as well as the calculated X-ray powder diffraction pattern based on the atomic positions given in Table 3.

Prior to characterization by X-ray powder diffraction, the sample was calcined at 540° C. for 6 hours in air. FIG. 1 depicts the X-ray powder diffraction pattern of a calcined sample of CIT-1. This X-ray powder diffraction pattern was indexed as monoclinic with unit cell parameters a=22.62 Å, b=13.28 Å, c=12.38 Å, β=68.9°. The diffraction peaks were individually deconvoluted and indexed as shown in Tables 1 and 1A. The atomic structure of the zeolite was solved giving the estimated atomic positions for silicon and oxygen shown in Table 3. The agreement between the calculated and experimental X-ray powder diffraction patterns indicate that the proposed structure is correct. The structure of CIT-1 is illustrated in "ball and stick" form in FIGS. 3A and 3B.

TABLE 3

Positional parameters for CIT-1

| Atom | x | y | z |
|------|------|------|------|
| Si1  | 0.07 | 0.12 | 0.51 |
| Si2  | 0.15 | 0.19 | 0.26 |
| Si3  | 0.07 | 0.12 | 0.73 |
| Si4  | 0.29 | 0.11 | 0.11 |
| Si5  | 0.29 | 0.11 | 0.85 |
| Si6  | 0.06 | 0.12 | 0.11 |
| Si7  | 0.16 | 0.19 | 0.86 |
| O1   | 0.07 | 0.00 | 0.53 |
| O2   | 0.08 | 0.18 | 0.62 |
| O3   | 0.12 | 0.15 | 0.39 |
| O4   | 0.00 | 0.15 | 0.50 |
| O5   | 0.21 | 0.12 | 0.18 |
| O6   | 0.09 | 0.16 | 0.21 |
| O7   | 0.16 | 0.31 | 0.25 |
| O8   | 0.07 | 0.00 | 0.71 |
| O9   | 0.01 | 0.16 | 0.84 |
| O10  | 0.14 | 0.14 | 0.76 |
| O11  | 0.31 | 0.00 | 0.12 |
| O12  | 0.30 | 0.13 | 0.97 |
| O13  | 0.33 | 0.19 | 0.16 |
| O14  | 0.22 | 0.13 | 0.86 |
| O15  | 0.32 | 0.00 | 0.81 |
| O16  | 0.07 | 0.00 | 0.11 |
| O17  | 0.10 | 0.17 | 0.99 |

ªSpace group C 2/m (12), a = 22.62 Å, b = 13.28 Å, c = 12.38 Å, β = 68.9°.

EXAMPLE 4

Preparation of CIT-1

The same experiment was set up as in Example 2, except that the crystallization temperature was 150° C. The experiment was run under analogous conditions, but the required time of crystallization was longer. Instead of 7 days, a total of about 60 days was required. The product was determined to be CIT-1 by X-ray diffraction.

EXAMPLE 5

Preparation of CIT-1

The same experiment was set up as in Example 2 except that boron content was increased by adding 0.1 g of $Na_2B_4O_7$.10 $H_2O$. This produced a $SiO_2/B_2O_3$ ratio of 25, compared with a value of 50 in Example 2. No crystals of as-synthesized boron zeolite beta were added to the synthesis gel, unlike Example 2. The crystallization time was 29 days at 150° C. The product was determined to be CIT-1 by X-ray diffraction. The pattern is tabulated in Table 4.

TABLE 4 d-spacing for as synthesized CIT-1 (Example 5).

| 2θ | d/(A) | 100 × I/I$_o$ |
| --- | --- | --- |
| 7.69 | 11.48 | 25 |
| 7.88 | 11.21 | 66 |
| 8.38 | 10.54 | 2 |
| 8.87 | 9.96 | 5 |
| 9.08 | 9.73 | 24 |
| 13.27 | 9.67 | 13 |
| 14.25 | 6.21 | 5 |
| 15.38 | 5.76 | 10 |
| 15.76 | 5.62 | 10 |
| 16.16 | 5.48 | 4 |
| 16.81 | 5.27 | 3 |
| 18.23 | 4.86 | 5 |
| 19.82 | 4.77 | 20 |
| 20.49 | 4.33 | 85 |
| 21.51 | 4.13 | 38 |
| 22.10 | 4.02 | 100 |
| 22.97 | 3.87 | 56 |
| 23.15 | 3.84 | 96 |
| 24.15 | 3.68 | 7 |
| 24.43 | 3.64 | 10 |
| 25.34 | 3.51 | 9 |
| 25.44 | 3.49 | 7 |
| 26.70 | 3.34 | 14 |
| 26.84 | 3.32 | 30 |

EXAMPLE 6

Calcination of CIT-1

Figure 4:
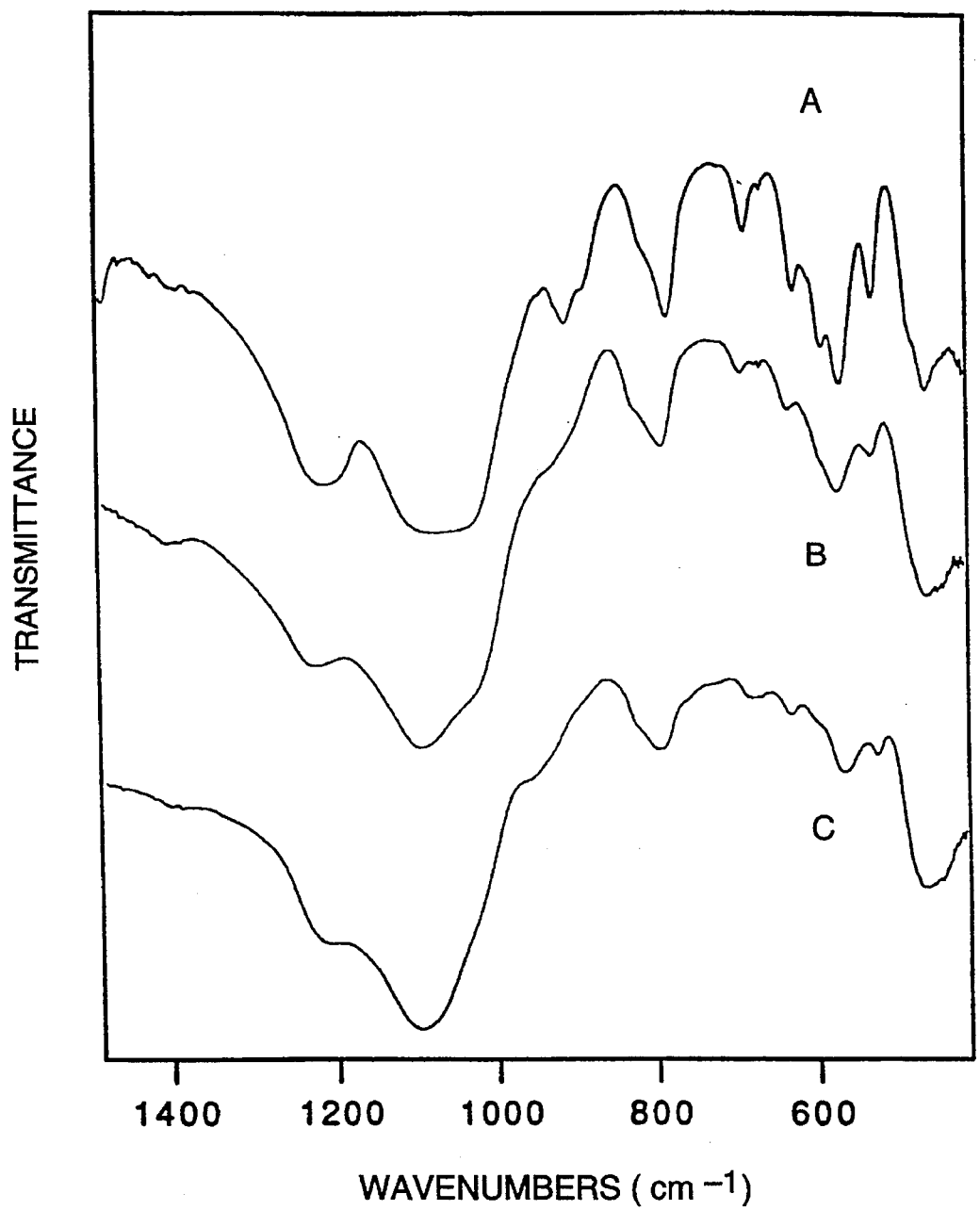
FIG. 4 shows the infrared spectra of as synthesized CIT-1 (A), calcined CIT-1 (B) and CIT-1 after treatment with $Al(NO_3)s$ (C).

The product of Example 2 was calcined as follows: the sample was heated in air from room temperature to 540° C. at a heating rate of 5° C. per minute. The sample was maintained at 540° C. for four more hours. The calcined sample had the X-ray diffraction lines indicated in Tables 1 and 1A. FIG. 4, lines labelled A and B, shows the infrared spectra of the samples before and after calcination.

EXAMPLE 7

Treatment With Aluminum Nitrate Solution

An experiment was run to exchange aluminum for boron within the CIT-1 catalyst in order to increase the number of acid sites. The calcined CIT-1 material was treated at room temperature with a 0.01 N HCl solution for 12 hours to remove the boron incorporated in the framework (solid:solution ratio 1:50 by weight). The filtered solid was then stirred in an Al(NO$_3$)$_3$.9 H$_2$O solution under reflux conditions for 12 h to introduce aluminum into the framework of CIT-1. The zeolite: Al(NO$_3$)$_3$.9H$_2$O:H$_2$O ratios were 1:2:50. After exchange, the product is filtered, washed and calcined again to 540° C. The infrared spectra of the starting sample, the calcined material before aluminum treatment and the treated material are shown in FIG. 4 as lines A, B and C respectively. A comparison of these data indicates that boron has been removed.

The calcined sample of aluminum CIT-1 was also characterized by the physical adsorption of nitrogen. The micropore volume was 0.20 cc/g of nitrogen.

EXAMPLE 8

Characterization of the acid properties of CIT-1 by ammonia temperature programmed desorption.

The acidic properties of CIT-1 materials were characterized using temperature programmed desorption (TPD) of ammonia. The experiments were carried out in a flow-type apparatus equipped with a fixed bed and a thermal conductivity detector. Prior to the NH$_3$ TPD experiments, 300 mg of the sample treated as in Example 7 were dehydrated in situ in the TPD system in a helium flow of 5 l/h at 600° C. at a heating rate of 5° C./min. Pure ammonia, with a flow rate of 3 l/h was passed through the sample at 150° C. for 15 min. The sample was subsequently purged with helium at the same temperature for 1 h to remove the physisorbed ammonia. The ammonia TPD was performed under a helium flow of 5 l/h from 150° to 600° C. with a heating rate of 10° C./min and kept at the final temperature for 30 min. Two desorption peaks were observed at 280° C. and 400° C. indicating the presence of two kinds of acid sites in the zeolite sample. For comparison, a sample of the commercial zeolite ZSM-5 treated in the same form, showed also two peaks at 260° C. and 450° C.

EXAMPLE 9

Catalytic activity of acidic zeolite CIT-1 in n-butane cracking reaction was carried out in a flow-type system equipped with a fixed bed reactor. Prior to the cracking experiments, 200 mg of the sample treated as described in Example 7 were dehydrated in situ in the reactor system in a helium flow of 5 l/h at 600° C., after heating from room temperature at a heating rate of 5° C./min. A gaseous mixture of n-butane and helium (20 vol % n-butane) was used for the reactions. The reactions were conducted at 500° C. under atmospheric pressure with a total gas flow of 2 l/h. The reactant and products were analyzed with an on-line gas chromatograph using a flame ionization detector and a 50m long capillary column that contained cross-linked methyl silicone gum as stationary phase. The conversion for the acid zeolite CIT-1 was 18% over a period of more than 15 hours. For comparison, a sample of ZSM-5 treated in a similar form showed a conversion of 41% over a similar period of time.

While the present invention is disclosed by reference to the aforementioned examples, it is to be understood that these examples are intended in an illustrative rather than limiting sense, as it is contemplated that modifications will readily occur to those skilled in the art, within the spirit of the invention and the scope of the appended claims.

What is claimed is:

1. A zeolite having a mole ratio greater than about 20:1 of a first oxide selected from silicon oxide, germanium oxide, and mixtures thereof to a second oxide comprising boron oxide; wherein said zeolite has, after calcination, the X-ray diffraction lines of Table 1.

2. A zeolite in accordance with claim 1 wherein said zeolite contains greater than 100 ppm of boron.

3. A zeolite in accordance with claim 1 wherein said second oxide further comprises a member of the group consisting of aluminum oxide, gallium oxide, iron oxide, titanium oxide, vanadium oxide and mixtures thereof.

4. A zeolite in accordance with claim 3 wherein said zeolite contains greater than 100 ppm of boron and a member of the group consisting of aluminum, gallium, iron, titanium, vanadium and mixtures thereof.

5. A zeolite in accordance with claim 1, wherein the amount of boron is between 1.5% and 0.3% by weight.

6. A zeolite in accordance with claim 5, wherein the amount of boron is about 0.7% by weight.

7. A zeolite having a composition, as synthesized and in the anhydrous state, in terms of mole ratios of oxides as follows:

(1.0 to 5) Q$_2$O:(0.1 to 1.0) M$_2$O :W$_2$O$_3$: (greater than 20) YO$_2$ wherein M is an alkali metal cation, W is selected from boron, or mixtures of boron with one or more of aluminum, gallium, iron, titanium and vanadium, Y is selected from silicon, germanium, and mixtures thereof, Q is N,N,N-trimethyl cis-myrtanyl ammonium ion; said zeolite having, after calcination, the X-ray diffraction lines of Table 1.

8. A zeolite in accordance with claim 7 wherein the N,N,N-trimethyl cis-myrtanyl ammonium ion is derived from

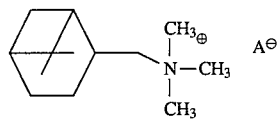

wherein A$^-$ is an anion which is not detrimental to the formation of the zeolite.

9. A zeolite in accordance with claim 8 wherein A$^-$ is hydroxide.

10. A zeolite having a mole ratio greater than about 20:1 of a first oxide selected from silicon oxide, germanium oxide and mixtures thereof to a second oxide selected from aluminum oxide, gallium oxide, iron oxide, titanium oxide, vanadium oxide and mixtures thereof, wherein said zeolite has, after calcination, the X-ray diffraction lines of Table 1.

11. A zeolite in accordance with claim 10 wherein said first oxide is silicon oxide.

12. A zeolite in accordance with claim 11 wherein said second oxide is aluminum oxide.

13. A method for preparing the zeolite of claim 1 comprising:

(a) preparing an aqueous mixture, wherein the aqueous mixture has a composition in terms of mole ratios of oxides of

| | |
|---|---|
| YO$_2$/W$_2$O$_3$ | 20–200 |
| OH/YO$_2$ | 0.10–1.0 |
| Q/YO$_2$ | 0.05–0.50 |
| M$^+$/YO$_2$ | 0.05–0.50 |
| Q/Q+M$^+$ | 0.30–0.80 | wherein M is an alkali metal cation, W is selected from boron, or mixtures of boron with one or more of aluminum, gallium, iron, vanadium and titanium, Y is selected from silicon, germanium, and mixtures thereof, and Q is N,N,N-trimethyl cis-myrtanyl ammonium ion;

(b) maintaining the mixture under sufficient crystallization conditions until crystals are formed; and (c) recovering the crystals.

14. A method for preparing the zeolite according to claim 13 wherein step b comprises the step of maintaining the temperature of said mixture at at least 100° C.

15. A method in accordance with claim 13 wherein the N,N,N-trimethyl cis-myrtanyl ammonium ion is derived from

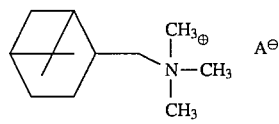

wherein A$^-$ is an anion which is not detrimental to the formation of the zeolite.

16. The method of claim 15 wherein the anion is hydroxide.

17. A process for converting hydrocarbons comprising contacting a hydrocarbonaceous feed at hydrocarbon converting conditions with a catalyst comprising the zeolite of claim 1.

18. A process for converting hydrocarbons comprising contacting a hydrocarbonaceous feed at hydrocarbon converting conditions with a catalyst comprising the zeolite of claim 10.

19. A catalytic cracking process comprising contacting a hydrocarbon feedstock in a reaction zone under catalytic cracking conditions in the absence of added hydrogen with a catalyst comprising the zeolite of claim 1.

20. A catalytic cracking process comprising contacting a hydrocarbon feedstock in a reaction zone under catalytic cracking conditions in the absence of added hydrogen with a catalyst comprising the zeolite of claim 10.

21. A process to convert paraffins to aromatics which comprises contacting paraffins with a catalyst comprising the zeolite of claim 1.

22. A process to convert paraffins to aromatics which comprises contacting paraffins with a catalyst comprising the zeolite of claim 10.

\* \* \* \* \*